United States Patent [19]

Oono et al.

[11] Patent Number: 5,151,752

[45] Date of Patent: Sep. 29, 1992

[54] METHOD OF MEASURING REFRACTIVE INDICES OF LENS AND SAMPLE LIQUID

[75] Inventors: Masahiro Oono; Tohru Chiba, both of Tokyo, Japan

[73] Assignee: Asahi Kogaku Kogyo K.K., Tokyo, Japan

[21] Appl. No.: 707,438

[22] Filed: May 28, 1991

Related U.S. Application Data

[63] Continuation of Ser. No. 609,845, Nov. 7, 1990, abandoned, which is a continuation of Ser. No. 519,355, May 8, 1990, abandoned, which is a continuation of Ser. No. 367,290, Jun. 16, 1989, abandoned.

[30] Foreign Application Priority Data

| Jun. 16, 1988 | [JP] | Japan | 63-149831 |
| Jun. 27, 1988 | [JP] | Japan | 63-158992 |
| Jun. 27, 1988 | [JP] | Japan | 63-158993 |
| Jul. 1, 1988 | [JP] | Japan | 63-165210 |
| Jul. 1, 1988 | [JP] | Japan | 63-165211 |

[51] Int. Cl.$^5$ .......................... G01B 9/00; G01B 11/00
[52] U.S. Cl. ............................... 356/128; 356/124; 356/361
[58] Field of Search ............. 356/124-134, 356/345, 73.1, 361, 362; 350/15, 162.2, 444, 482, 416; 528/26, 26.5, 29; 556/442, 446, 450, 462; 359/652, 665

[56] References Cited

U.S. PATENT DOCUMENTS

| 4,361,402 | 11/1982 | Costa | 356/128 |
| 4,565,449 | 1/1986 | Grego | 356/361 |
| 4,759,628 | 7/1988 | Tatsuno et al. | 356/349 |

OTHER PUBLICATIONS

"Polyolefin System Resin," vol. 38, No. 7, pp. 41-44.
"Refractive Index of Plastic Lens," Optics, vol. 12, No. 6, pp. 460-463, Dec. 1983.

Primary Examiner—Richard A. Rosenberger
Assistant Examiner—Hoa Pham
Attorney, Agent, or Firm—Sughrue, Mion, Zinn, Macpeak & Seas

[57] ABSTRACT

A method of measuring a refractive index distribution of a lens is disclosed which comprises, immersing a glass sample and a lens under test within a matching fluid whose refractive index differs slightly from that of the glass to be tested, the glass sample having a refractive index and a shape which are both known and the lens to be tested having an unknown refractive index but a known shape, allowing coherent light to pass through the glass sample and the lens under test; superposing the transmitted light wave on a reference light wave to generate interference fringes, outputting the intensity distribution of interference fringes that are generated by the light wave that has passed through the glass sample, determining the refractive index of the matching fluid on the basis of the resulting output, outputting the intensity distribution of interference fringes that are generated by the light wave that has passed through the lens under test; separating from the resulting output the defocus term and aberration terms in the polynomial which expresses the produced interference fringes; determining the average refractive index of the lens under test from the separated defocus term and the refractive index of the matching fluid; and determining the refractive index distribution of the lens under test from the aberrations terms.

39 Claims, 8 Drawing Sheets

METHOD OF MEASURING REFRACTIVE INDICES OF LENS AND SAMPLE LIQUID

This is a continuation application of pending prior parent application Ser. No. 07/609,845 filed on Nov. 7, 1990, which is a continuation of Ser. No. 07/519,355 filed May 8, 1990, which is a continuation of Ser. No. 07/367,290 filed Jun. 16, 1989, all now abandoned.

BACKGROUND OF THE INVENTION

The present invention relates to a method of measuring the refractive index of lenses and sample liquid. More particularly, the present invention relates to a method suitable for measuring the refractive indices and refractive index distribution of plastic lenses.

The present invention also relates to a matching fluid that is to be used in optical testing such as measurements of the refractive indices of lenses. The present invention also relates to an interferometer that employs said matching fluid or liquid.

The use of plastic lenses has expanded recently in order to meet various needs such as demands for lighter lenses, reduction in production cost and increased use of aspherical lenses. One big problem with plastic lenses is that they are not as stable as glass lenses in physical properties and that their refractive indices and distribution thereof will experience great variations during lens manufacture. It is therefore necessary to measure the refractive indices of individual plastic lenses and their distribution after molding. But these measurements should be nondestructive and hence are difficult to perform on an industrial scale. The difficulty is even greater in the case of aspherical lenses.

The refractive index of plastic lenses has conventionally been measured by the following procedure using an apparatus which is generally in the form of a Mach-Zehnder interferometer. Rays of light are used as reference light of plane waves, and a lens to be tested is set in the optical path of another set of rays, with the lens being immersed in a matching fluid whose refractive index is substantially equal to that of the lens under test. A glass sample with a known refractive index which is close to that of the lens under test is also set as a reference for refractive index measurement, with said glass sample being immersed in the same matching fluid. A test assembly comprising these components is placed in rays of light (serving as reference light of plane waves) in a Mach-Zehnder interferometer and the number of interference fingers produced is counted. The difference in sample thickness within the range where N interference fringes are observed is measured and the refractive index of the lens under test is determined on the basis of the measured value.

This method, however, has suffered from the problem that the refractive index of the matching fluid will vary with factors such as temperature variations. Thus, when temperature changes, the range within which N interference fringes appear will also change, making it necessary to perform another measurement of sample thickness in the affected area. A further problem is that nonuniformity in the refractive index distribution of a lens will produce irregularly shaped interference fringes, causing difficulty in obtaining the correct meaning of "N interference fringes". In other words, refractive index measurements under these circumstances have involved considerable difficulty in attaining reproducible results by quantitative interpretation. This has been a major cause of the difficulty encountered in attempts to automatic refractive index measurements.

SUMMARY OF THE INVENTION

An object, therefore, of the present invention is to solve these problems of the prior art and to provide a method by which the refractive index and index distribution of a lens can be measured without destroying it and which also facilitates quantitative interpretation and automation of measurements.

In order to attain this object, the method of the present invention measures the refractive index and index distribution of a lens by the following steps: immersing a glass sample and a lens under test within a matching fluid whose refractive index differs slightly from that of the glass to be tested, said glass sample having a refractive index and a shape which are both known and said lens to be tested having an unknown refractive index but a known shape; allowing coherent light to pass through said glass sample and said lens under test; superposing the transmitted light wave on a reference light wave to generate interference fringes; outputting the intensity distribution of interference fringes that are generated by the light wave that has passed through said glass sample; determining the refractive index of said matching fluid on the basis of the resulting output; outputting the intensity distribution of interference fringes that are generated by the light wave that has passed through said lens under test; separating from the resulting output the defocus term and aberration terms in the polynomial which expresses the produced interference fringes; determining the average refractive index of said lens under test from the separated defocus term and the refractive index of the matching fluid; and determining the refractive index distribution of said lens under test from said aberration terms.

Matching fluids used in optical testing such measurements of the refractive indices of lenses are required to satisfy the following conditions:

(a) that a desired refractive index be readily attainable by mixing a plurality of liquid components;

(b) that the resulting fluid mixture be highly homogeneous and stable;

(c) that the fluid mixture be resistant to temperature variations in terms of such characteristics as refractive index and viscosity; and (d) that the fluid mixture not attack the object under test, have no malodor or present no safety hazards to humans.

Matching fluids that satisfy all of these conditions are fairly easy to obtain if the object under test is made of glass. However, if the object under test is made of a plastic material, most of the matching fluids available today are unsatisfactory since they attack plastic materials. Some fluids that do not attack plastic materials have the disadvantage that they cannot be mixed uniformly with other fluids having different refractive indices to attain a desired refractive index. It has therefore been extremely difficult to obtain matching fluids that are acceptable for use in testing plastic lenses.

A practice that has been previously adopted to deal with this situation is to use a matching fluid that is prepared by mixing fluids of an identical type that will not attack an object to be tested and that have different refractive indices. If two fluids are of entirely the same type, they can be mixed to yield an optically uniform product. However, with such fluids of an identical type, the range of refractive indices that can be attained is so narrow that the objects that can be tested are extremely limited.

An object, therefore, of the present invention is to solve these problems of the prior art and to provide matching fluids that can be used in testing not only glass lenses but also plastic lenses and which yet allow for refractive indices to be adjusted over a broad range. Another object of the present invention is to provide an interferometer that uses such improved matching fluids.

An object of the present invention can be attained by a matching fluid consisting of one or more dimethyl silicone oils having refractive indices within the range of 1.350–1.450 which are mixed with one or more phenylmethyl silicone oils having refractive indices within the range of 1.480–1.630.

An object of the present invention can be attained by an interferometer comprising:

a matching fluid consisting of one or more dimethyl silicone oils having refractive indices within the range of 1.350–1.450 which are mixed with one or more phenylmethyl silicone oils having refractive indices within the range of 1.480–1.630;

a transparent cell for accommodating said matching fluid in which an object under test is to be immersed;

coherent light illuminating means that illuminates said transparent cell with coherent light; and reference light illuminating means that provides an illumination of reference light in such a way that it is superposed on the coherent light passing through said transparent cell.

Polymethyl methacrylate (or simply referred to as an acrylic resin) is one of the most common plastic materials that are employed in optical lenses. Silicone oil based fluids will not attack this acrylic resin at all, nor do they attack most of other kinds of plastic materials in optical use. Needless to say, glass materials are resistant to silicone oil based fluids, which are colorless, odorless and nontoxic to humans.

The acrylic resin has a refractive index of 1.491, which is lower than the refractive indices of most other plastics in optical use (the lowest refractive index achievable by optical plastics is on the order of 1.470). On the higher side, polystyrene has a refractive index of 1.590.

In refractive index measurements, it is common practice to adjust the refractive index of a matching fluid to a value that is substantially equal to that of an an object to be tested. To this end, the matching fluid must contain two liquid components, one having a higher refractive index than the object under test and the other having a lower refractive index. Among various silicone oil based fluids, dimethyl silicone oils typically have refractive indices of about 1.400, which may range from 1.350 to 1.450, whereas phenylmethyl silicone oils have refractive indices that are typically on the order of 1.500–1.570 and that may range from 1.480 to 1.630. Thus, by mixing one or more dimethyl silicone oils with one or more phenylmethyl silicone oils, matching fluids can be produced whose refractive index latitude is great enough to attain matching with any kinds of plastic materials to be tested.

Dimethyl silicone oils are not completely identical in composition to phenylmethyl silicone oils, but since their compositions are so close to each other that they are highly miscible and can be readily mixed into a homogeneous state.

A matching fluid made by mixing dimethyl silicone and phenylmethyl silicone oils is loaded into a transparent cell, an object to be tested is immersed in the matching fluid, the cell is illuminated with coherent light, and an illumination of reference light is superposed on the coherent light passing through the cell, thereby producing observable interference fringes. If one of the two liquid components of the matching fluid (i.e., dimethyl silicone oil or phenylmethyl silicone oil) is selectively dripped into the matching fluid, the appearance of interference fringes will change and one may simply adjust the refractive index of the matching fluid so as to attain a predetermined appearance of the interference fringes.

Needless to say, the objects that can be tested by this method are not limited to plastic lenses, and glass lenses can also be used.

According to the invention, there is provided a method of measuring a refractive index distribution of a lens, comprising the following steps: immersing a glass sample and a lens under test within a matching fluid whose refractive index differs slightly from that of the glass to be tested, said glass sample having a refractive index and a shape which are both known and said lens to be tested having an unknown refractive index but a known shape; allowing coherent light to pass through said glass sample and said lens under test; superposing the transmitted light wave on a reference light wave to generate interference fringes; outputting the intensity distribution of interference fringes that are generated by the light wave that has passed through said glass sample; determining the refractive index of said matching fluid on the basis of the resulting output; outputting the intensity distribution of interference fringes that are generated by the light wave that has passed through said lens under test; separating from the resulting output the defocus term and aberration terms in the polynomial which expressed the produced interference fringes; determining the average refractive index of said lens under test from the separated defocus term and the refractive index of the matching fluid; and determining the refractive index distribution of said lens under test from said aberration terms.

According to another aspect of the invention, there is provided a method of measuring the refractive index of a lens by the following steps: immersing in a first matching fluid a glass sample having a refractive index and a shape which are both known and a lens under test whose refractive index and shape are both unknown; allowing coherent light to pass through said glass sample and said lens under test; superposing the transmitted light wave on reference light wave to generate interference fringes; outputting the intensity distribution of interference fringes that are generated by the light wave that has passed through said glass sample; determining the refractive index of said first matching fluid on the basis of the resulting output; outputting the intensity distribution of interference fringes that are generated by the light wave that has passed through said lens under test; determining from the resulting output a first polynomial that expresses said interference fringes; subsequently immersing said glass sample and said lens under test in a second matching fluid having a refractive index slightly different from that of the first matching fluid; allowing said coherent light to pass through said glass sample and said lens under test; superposing the transmitted light wave on reference light wave to generate interference fringes; outputting the intensity distribution of interference fringes that are generated by the light wave that has passed through said glass sample; determining the refractive index of said second matching fluid on the basis of the resulting output; outputting the intensity distribution of interference fringes that are generated by the light wave that has passed through said lens under test; determining from the resulting output a second polynomial that expresses said interference fringes; determining the shape of said lens under test from the refractive indices of the first and second matching fluids using the first and second polynomials; separating the defocus term from the aberration terms in said first or second polynomial; determining the average refractive index of said lens under test from the separated defocus term and from the refractive index of said first or second matching fluid; and determining the refractive index distribution of said lens under test from said aberration terms.

According to the invention, there is provided a method of measuring a refractive index distribution of a lens, in an interferometer wherein a lens under test is immersed into sample liquid whose refractive index differs slightly from that of the test lens, and coherent light is allowed to pass through said test lens to superpose with reference light to form a fringe, said method characterized by comprising:

providing in said interferometer a fine angular adjustment means for finely adjusting an expansion angle for at least one of transmitted light and reference light from parallel beam to non-parallel beam;

adjusting said fine angular adjustment means to eliminate fringe components generated due to a difference between the refractive index of said test lens and the refractive index of said sample liquid; and measuring the refractive index of said test lens in accordance with a condition of the interference fringe measured in said adjusting step.

According to still another aspect of the invention, there is provided a matching fluid consisting of one or more dimethyl silicone oils having refractive indices within the range of 1.350-1.450 which are mixed with one or more phenylmethyl silicone oils having refractive indices within the range of 1.480-1.630.

An interferometer comprising:

a matching fluid consisting of one or more dimethyl silicone oils having refractive indices within the range of 1.350-1.450 which are mixed with one or more phenylmethyl silicone oils having refractive indices within the range of 1.480-1.630;

a transparent cell for accommodating said matching fluid in which an object under test is to be immersed;

coherent light illuminating means that illuminates said transparent cell with coherent light; and reference light illuminating means that provides an illumination of reference light in such a way that it is superposed on the coherent light passing through said transparent cell.

DETAILED DESCRIPTION OF THE INVENTION

Figure 1:
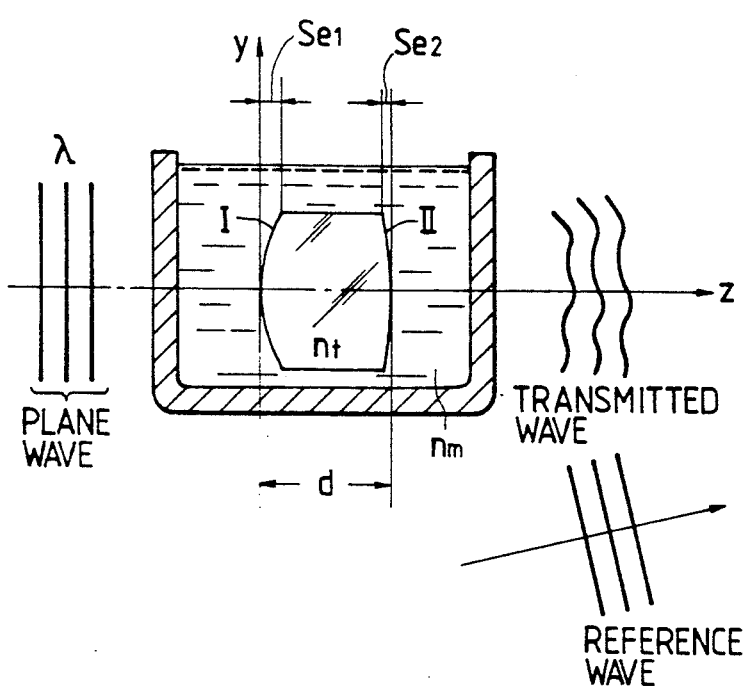
FIGS. 1 and 2 are diagrams illustrating the principle of measurement by the method of the present invention.
Figure 2:
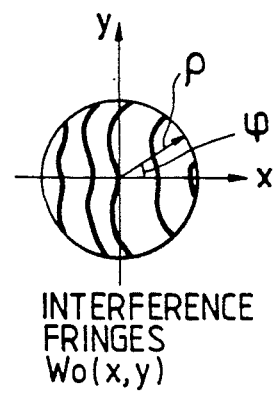

For theoretical discussion, assume the case where plane wave having a wavelength $\lambda$ is transmitted through a lens under test that is immersed in a matching fluid whose refractive index $n_m$ is substantially equal to the refractive index, $n_t$, of the lens, with the result that interference fringes $W_o(x, y)$ are produced by the transmitted light wave and reference light wave (see FIGS. 1 and 2).

The shape of the lens under test is known (its design and measured values are known). If the shapes of the two surfaces, I and II, are expressed by $Z_1 = S_1(x, y)$ and $Z_2 = S_2(x, y)$, respectively, with the lens thickness across the center being written as d, the sum of sags on both surfaces is expressed by:

$$Sag(x, y) = S_1(x,y) + S_2(x, y) \qquad (1).$$

If refractive index $n_t(x, y)$ is divided into two portions, i.e., average refractive index $n_{to}$ and refractive index distribution, $\Delta n_t(x,y)$, then $$W_o(x,y) = Sag(x,y)\cdot[n_{to} - n_m] + [d - Sag(x,y)]\Delta n_t(x,y) \qquad (2)$$

From eq. (2), one can see that if the refractive index $n_m$ of the matching fluid is measured, $W_o(x,y)$ will become a function of only two variables, $n_{to}$ and $\Delta n_t(x, y)$. However, it is generally impossible to determine these two parameters as separate entities.

If eq. (2) is expanded in the Zernike polynomial which is a common expansion of wavefront aberration, then $$\begin{aligned}W_0(w,y) &= Sag(x,y)\cdot[n_{to} - n_m] + \\ &\quad [d - Sag(x,y)]\Delta n_t(x,y) \\ &= C_1 + C_2\rho\cos\psi + C_3\rho\sin\psi + \\ &\quad C_4(2\rho^2 - 1) + C_5\rho^2\cos 2\psi + \ldots\end{aligned}$$

where $C_2\rho \cos \psi$ and $C_3\rho \sin \psi$ are tilt terms, $C_4(2\rho^2 - 1)$ is a defocus term ($W_2$), and $C_5\rho^2 \cos 2\psi + \ldots$ are aberration terms (W). Since $[n_{to} - n_m]$ is supposed to be nearly equal to zero, $Sag(x,y)\cdot[n_{to}-n_m]$ can be approximated by a quadratic function, which is substantially equal to the defocus term ($W_2$).

Figure 3:
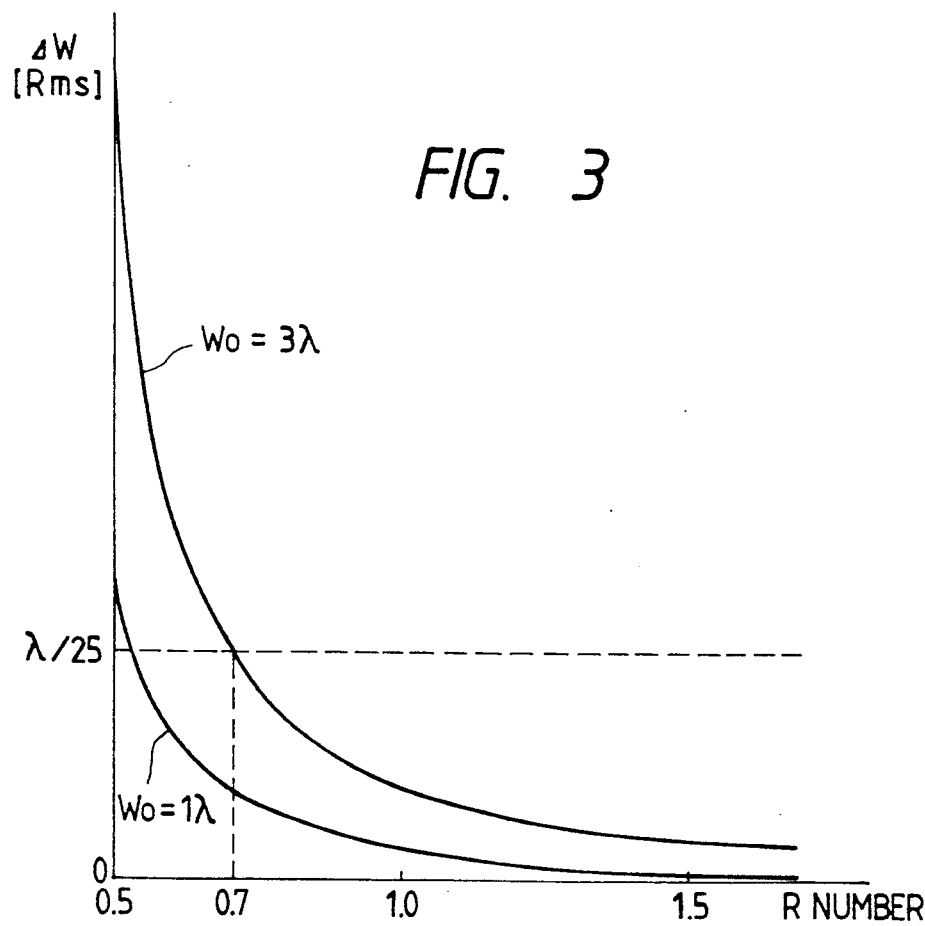
FIG. 3 is a graph illustrating the precision of measurement by the method of the present invention.

FIG. 3 is a graph showing the aberration term ($\Delta W$) vs the R number ($R=r/D$) of a lens with diameter D having a spherical surface ($r$=radius of curvature) on one side and a planar surface ($r=\infty$) on the other side but having no refractive index distribution, assuming that the matching fluid is conditioned to ensure that three interference fringes ($W_o=3\lambda$) or one fringe ($W_o=1\lambda$) will be observable with the lens under test. If the threshold value of $\Delta W$ for reproducible reading of interference fringes (i.e., the resolution of fringes) is assumed to be $\lambda/25$ in terms of Rms, FIG. 3 shows that R should be equal to or smaller than 0.7 even in the case for observing three interference fringes. Hence, the resolving power of interference fringes is not attainable with lenses of most values of R number, and this means that all the components of observed interference fringes will be expressed by the defocus term ($W_2$). Thus, $[n_{to}-n_m]$ is determined from the defocus term $W_2$ in the observed (or read) fringe $W_o(x,y)$, and $\Delta n_t(x,y)$ is determined from aberration term (W), thus making it possible to separate the two parameters from each other, as expressed below:

$$n_{to} - n_m = \frac{\text{defocus term}}{Sag(x,y)} = \frac{2C_4}{(Se_1 + Se_2)}$$

$$\Delta n_t(x,y) = \frac{\text{aberration term}}{[d - Sag(x,y)]} = \frac{W(x,y)}{[d - Sag(x,y)]}$$

($Se_1$ and $Se_2$ denote Sag maxima on opposite surfaces of the lens as illustrated in FIG. 1).

In conclusion, the refractive index distribution of the lens under test is determined from the aberration terms in the Zernike polynomial, and if the refractive index of the matching fluid is known, the average refractive index of the lens under test can be determined from the defocus term in the same polynomial.

It should be noted here that the refractive index $n_m$ of the matching fluid can be determined from the refractive index and shape, which are both known, of the glass sample.

On the other hand, in accordance with another method of the present invention, a series of measurements are conducted using a first and a second matching fluid having slightly different refractive indices and the interference fringes produced with these matching fluids are analyzed to determine the amount of sag in the lens under test.

If the first and second matching fluids are supposed to have refractive indices $n_{m1}$ and $n_{m2}$ and if the interference fringes produced when first and second matching fluids are introduced are written as $W_{01}$ and $W_{02}$, then the following relationships will hold:

$$W_{01}(x,y)=Sag(x,y)\cdot[n_{to}-n_{m1}]+[d-Sag(x,y)]\Delta n_t(x,y) \quad (3)$$

$$W_{02}(x,y)=Sag(x,y)\cdot[n_{to}-n_{m2}]+[d-Sag(x,y)]\Delta n_t(x,y) \quad (4)$$

By subtracting eq. (4) from eq. (3), we obtain $$Sag(x,y) = \frac{W_{01}(x,y) - W_{02}(x,y)}{n_{m2} - n_{m1}} \quad (5)$$

Therefore, if $n_{m1}$ and $n_{m2}$ are known, the amount of sag in the lens under test can be determined from eq. (5).

Figure 4:
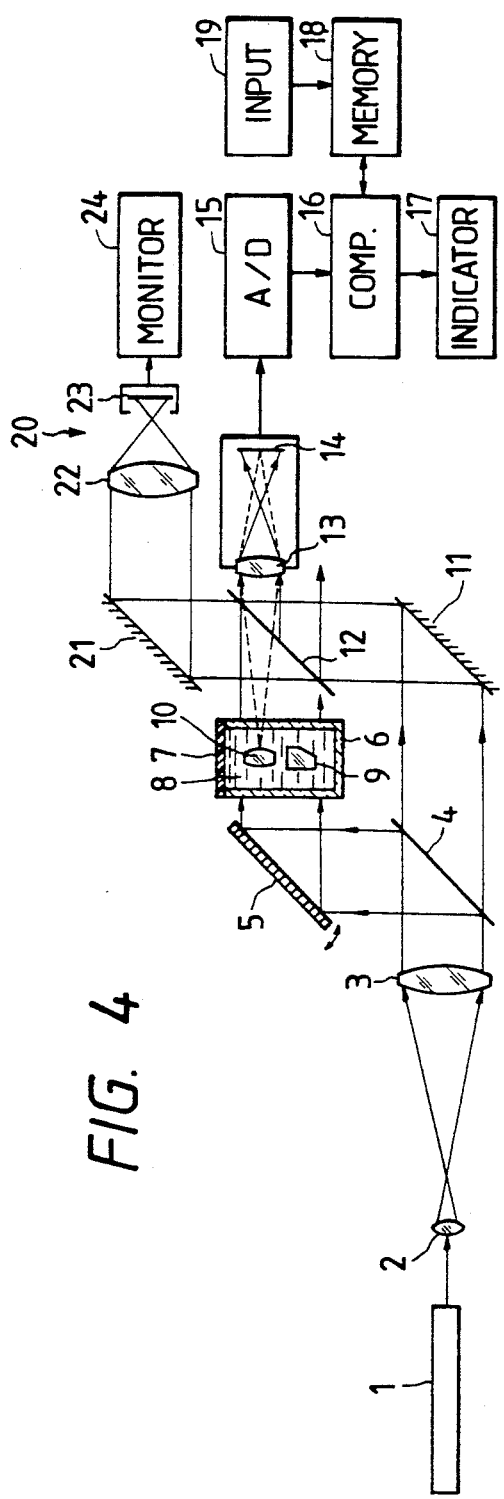
FIGS. 4-6 are diagrams showing an apparatus that may be used to implement the method of measurement of the present invention.

FIG. 4 shows a measuring apparatus that may be used to implement the method of the present invention. This apparatus is constructed basically as a Mach-Zehnder interferometer. Shown by 1 is a coherent light source which emits coherent light (wavelength, $\lambda$) and may be exemplified by a He-Ne laser light source. The rays of light emitted from the coherent light source 1 are expanded with an expander lens 2 and collimated by a collimator lens 3. Shown by 4 is a first half mirror and the parallel rays of light that are reflected from this half mirror 4 are again reflected from a movable mirror 5 for passage through a transparent cell 6. The movable mirror 5 can be tilted through desired small angles.

Figure 5:
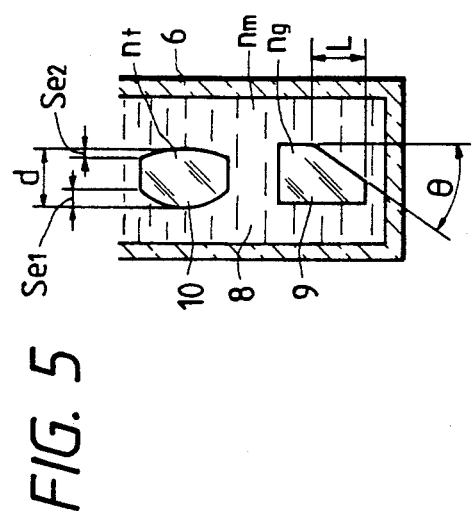

The transparent cell 6 is formed of undistorted glass and is furnished with a cover 7 that can be freely opened or closed. The transparent cell 6 contains a lens under test 10 which is immersed in a matching fluid 8. The matching fluid 8 is made of a mixture of a dimethyl silicone oil and a phenylmethyl silicone oil if the lens 10 is formed of a polymethyl methacrylate (or simply referred to as an acrylic resin). As shown more clearly in FIG. 5, a glass sample 9 whose refractive index $n_g$ and shape ($\theta$, L) are both known and the lens under test 10 whose refractive index $n_t$ is unknown but whose shape [d, Sag(x,y)] is known are juxtaposed within the matching fluid 8 in such a way that both members will be oriented perpendicular to the rays of light that are transmitted through the cell 8. The lens under test 10 is typically a plastic lens such as one being made of polymethyl methacrylate (or acrylic resin) but it should of course be understood that the method of the present invention is also applicable to lenses that are made of glass or some other materials.

The rays of light that have passed through the first half mirror 4 are reflected from a first fixed mirror 11, thence reflected by a second half mirror 12, and superposed on the light wave that has passed through the lens under test 10 or the glass sample 9. Interference fringes will then form as a result of the superposition of the two light waves and are focused on the screen of an imaging device 14 via a first imaging lens 13.

Figure 6:
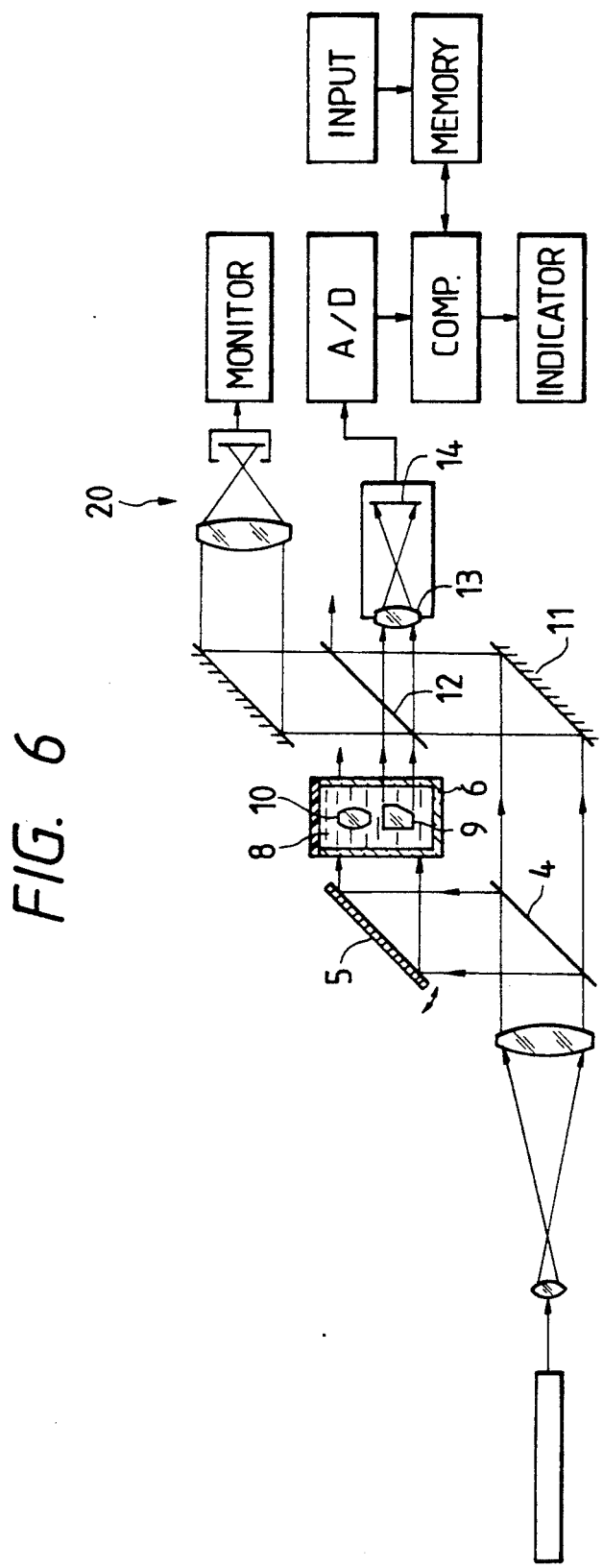

The first imaging lens 13 and the imaging device 14 are adapted to be movable enmasse vertically as viewed in FIG. 4. Thus, the first imaging lens 13 which is shown to oppose the lens under test 10 in FIG. 4 may be moved to a position at which it opposes the glass sample 9 as shown in FIG. 6.

Turning back to FIG. 4, the imaging device 14 may be composed of an array of 50×50 independent photoelectric transducers and the output terminal of the imaging device 14 is connected successively to an A/D converter 15, a digital arithmetic circuit 16 and a display unit 17. The arithmetic circuit 16 is connected successively to a memory 18 that stores the data necessary for performing arithmetic operations, and an input circuit 19 which is operated to enter known data. The arithmetic circuit 16 may be composed of a microcomputer and associated arithmetic units.

Shown by 20 is a viewing unit with which the inside of the transparent cell 6 can be observed. The viewing unit 20 is composed of a second fixed mirror 21 adapted to face the second half mirror 12, a second imaging lens 22, an imaging device 23 disposed at the focal point of the lens 22, and a television monitor 24.

The process of measuring the refractive index of lens 10 by the method of the present invention starts with entering known data into the input circuit 19. Known data (ng, θ, L) concerning the glass sample 9 is entered into the memory 18 for storage. Based on the known data [d, Sag(x,y)] concerning the shape of the lens 10, sag maxima (Se$_1$+Se$_2$) for opposite sides of the lens 10 and the thicknesses of various lens portions [d−Sag(x,y)] are computed in the arithmetic circuit 16 and the results are stored in the memory 18.

In the next step, the refractive index, $n_m$, of a the matching fluid 8 is adjusted to a value slightly different from the refractive index, $n_t$, of lens 10. The operator, looking at the television monitor 24, will perform the adjusting operation in such a way that the number of interference fringes that are produced with the light wave passing through the lens 10 will not exceed a certain value, say, three. More specifically, the cover 7 is removed from the cell 6, one of the two silicone oils that make up of the matching fluid 8 is dripped into the cell 6 by suitable means such as a dropping pipette, and the matching fluid 8 is stirred to mix the two components.

When a number of lenses of the same design value are subjected to consecutive measurements, the matching fluid 8 need be adjusted for refractive index ($n_m$) only once before the measurement is started.

Figure 7:
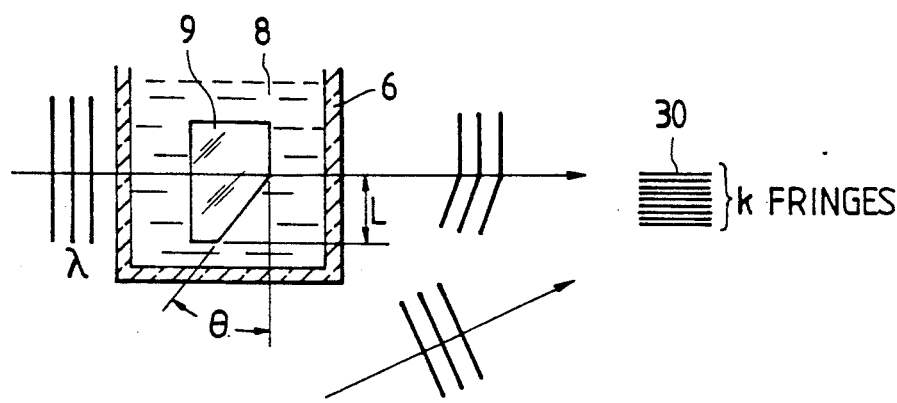
FIGS. 7-9 are diagrams showing the procedures of determining the refractive index of a matching fluid.

In the next step, the first imaging lens 13 is moved to a position where it faces the glass sample 9 as shown in FIG. 6. As a result, interference fringes 30 that are produced by superposition of reference light wave on the light wave passing through the glass sample 9 will be imaged on the imaging device 14 as shown in FIG. 7. Based on the output from the imaging device 14, the spatial frequency F of the fringes is computed with the arithmetic circuit 16. This may be accomplished by known discrete Fourier transform (DFT) but the use of fast Fourier transform (FFT) is preferred because of its capability for high-speed processing.

Figure 8:
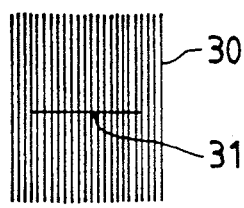
Figure 9:
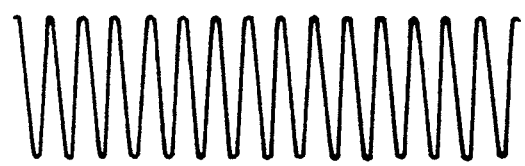

In the embodiment being discussed, a segment of a line 31 that is drawn perpendicular to the interference fringes 30 on the screen of imaging device 14 as shown in FIG. 8 is assumed, and based on the output of this segment, a brightness intensity distribution generally in the form of a sine wave as shown in FIG. 9 is computed. Based on the computed intensity distribution, the spatial frequency F of the interference fringes is computed by FFT to determine the refractive index, $n_m$, of the matching fluid 8. The arithmetic basis for these computations is as follows: since F=k/L and $(n_m-n_g)L\cdot\tan\theta=k\lambda$, $n_m=n_g+\lambda\cdot F/\tan\theta$. The value of $n_m$ thus determined is stored in the memory 18.

Figure 10:
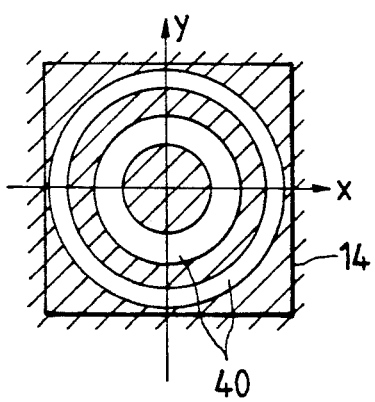
FIG. 10 is a diagram showing the interference fringes that are produced on the screen of an imaging device with a light wave that has passed through a lens under test.
Figure 10A:
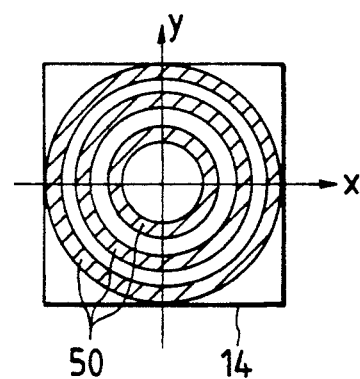
FIG. 10A is a diagram showing the modified interference fringes produced on the screen of an imaging device, following high precision fringe analysis, by a light wave that has passed through a lens under test.

In the next step, the first imaging lens 13 is moved to a position where it faces the lens 10 as shown in FIG. 4. Then, interference fringes 40 that are produced by superposition of a reference light wave on the light wave passing through the lens 10 will be focused on the screen of the device 14 as shown in FIG. 10. The output from the imaging device 14 is first subjected to high-precision fringe analysis in the arithmetic circuit 16, which produces a series of modified interference fringes 50, as shown in FIG. 10A. This analysis may be performed by a known spatial fringe scanning method with the fringes being tilted by rotating the movable mirror 5 through a small angle. After phase determination, expansion in a polynomial expression is performed in the arithmetic circuit 16. In the example being discussed, expansion may be in the Zernike polynomial.

After reading the refractive index ($n_m$) of the matching fluid 8 and sag maxima of lens 10 (Se$_1$+Se$_2$) from the memory 18, the average refractive index $n_{to}$ of lens 10 is determined from the defocus term in the polynomial using:

$$n_{to} - n_m = \frac{\text{defocus term}}{Se_1 + Se_2}$$

and the result is displayed on the display unit 17.

Also read from the memory 18 are the data on the thicknesses of various portions of the lens 10, [d−Sag(x,y)], and the refractive index distribution of lens 10, $\Delta n_t(x,y)$, is determined from the aberration terms (W) in the polynomial using:

$$\Delta n_t(x,y) = \frac{W(x,y)}{d - Sag(x,y)}$$

and the result is also displayed on the display unit 17.

Example of Measurement 1

Figure 11:
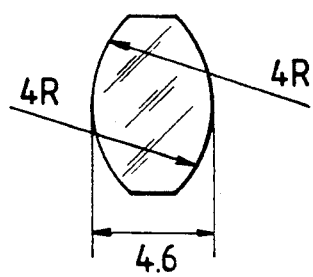
FIG. 11 is a diagram of a lens on which measurements are to be performed in Example of Measurement 1.

The refractive index and index distribution of a convex glass (BK 9) lens were measured. The shape of the lens is shown in FIG. 11; its thickness across the center was 4.6 mm and each convex surface had a curvature radius of 4 mm. When measured by a method other than that of the present invention using light having a wavelength (λ) of 632.8 nm, the refractive index of BK 9 was found to be 1.49255, with the refractive index distribution being considered to be substantially uniform in every part of the lens. The following were the results obtained when maximum sag was 1.2 mm (0.6×2), with the number of observed interference fringes being about 1.5λ:

Average refractive index: 1.4925

Peak in refractive index distribution: $0.174\times10^{-4}$.

This data shows that the method of the present invention was capable of very exact measurement of average refractive index, with extremely small errors being involved to provide a very narrow refractive index distribution.

Example of Measurement 2

Measurements were conducted on an acrylic (polymethyl methacrylate) lens by the method of the present invention, with the composition of a matching fluid being varied to provide different refractive indices. The results were as follows.

(1) When the matching fluid had a refractive index of 1.4901, the acrylic lens was found to have a refractive index of 1.4903 and the peak in refractive index distribution was at $0.511\times10^{-4}$.

(2) When the matching fluid had a refractive index of 1.4097, the acrylic lens was found to have a refractive index of 1.4902 and the peak in refractive index distribution was at $0.852\times10^{-4}$.

This data shows that variations in the composition of the matching fluid caused substantially no effects on the results of measurement.

Example of Measurement 3

Figure 12:
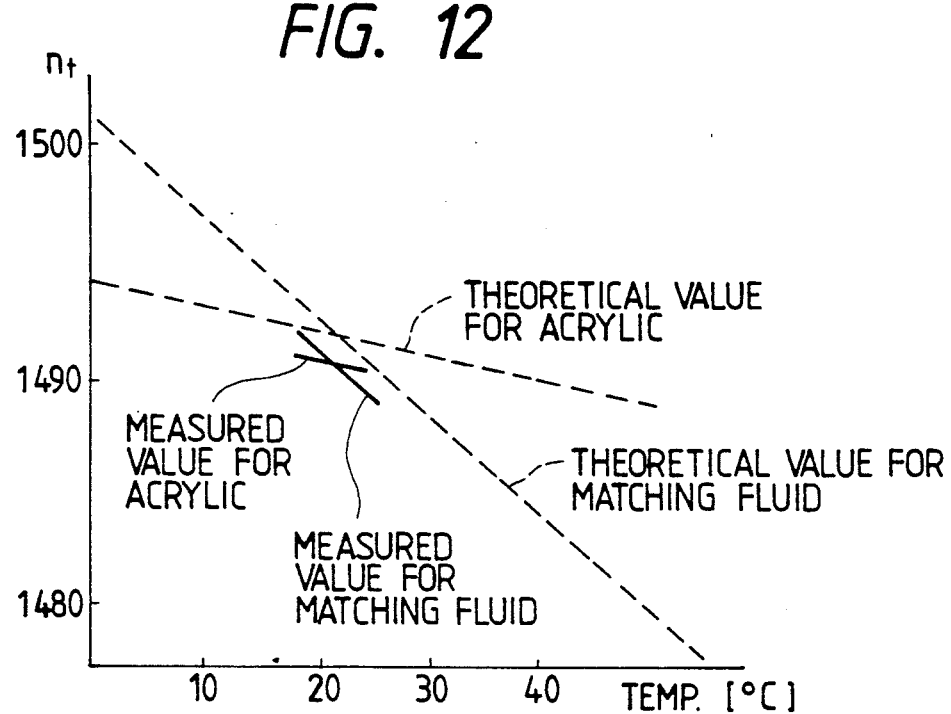
FIGS. 12 and 13 are graphs showing the results obtained in Example of Measurement 3.
Figure 13:
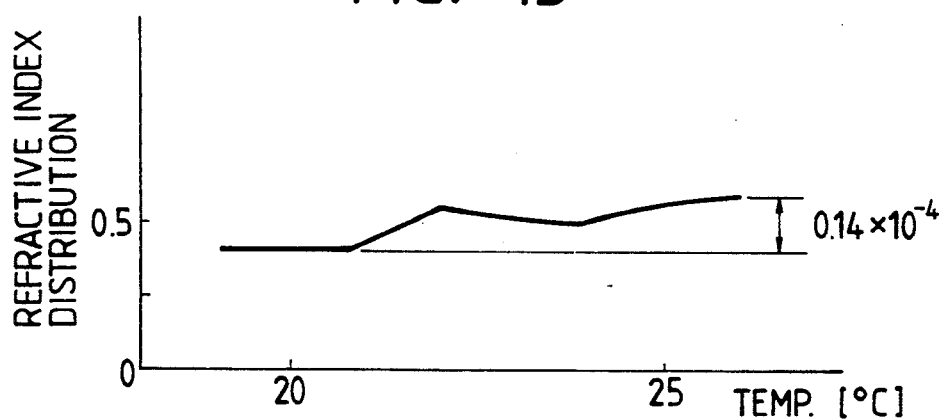

Measurements were conducted on an acrylic (polymethyl methacrylate) lens by the method of the present invention, with temperature being varied from 19° to 25° C. The results are shown in FIG. 12 (for average refractive index, $n_t$) and in FIG. 13 (refractive index distribution). As FIG. 12 shows, the measured refractive indices of the acrylic lens at different temperatures were in substantial agreement with the theoretical values for the same lens material (polymethyl methacrylate) at the d-line. Substantial agreement was also observed between the measured refractive indices of the matching fluid at different temperatures and the theoretical values for the same matching fluid (as measured with an Abbe refractometer). As FIG. 13 shows, the value of the peak in refractive index distribution was only $1.4 \times 10^{-5}$, indicating substantial absence of temperature dependency in the refractive index distribution measured by the method of the present invention.

In order to perform measurements by the method of the present invention, the lens to be tested needs only to be immersed in a matching fluid without destroying it. In addition, the average refractive index of the lens under test can be determined on the basis of the output for the intensity distribution of interference fringes by extracting the defocus term of the polynomial that represents the interference fringes, whereas the refractive index distribution of the lens is determined from the aberration terms of the same polynomial. Thus, the method of the present invention is capable of performing quantitative measurements of lens performance, which contributes to greater facility in automating the procedures of analysis.

In the foregoing method, a refractive index and a shape of the glass sample and a shape of the test lens are known to obtain the refractive index distribution of the test lens.

According to another aspect of the invention, it is possible to obtain the refractive index distribution of the test lens from the refractive index and shape of glass sample (unknown refractive index and unknown shape). In this case, the refractive index $n_{m1}$ of the first matching liquid is used in the same manner as described above.

The operation concerning the second matching liquid will be described. Now, the mixing rate of the matching liquid 8 is changed to be somewhat different from that of the first matching liquid. Also, in this case, one of the two silicone oils that make up the matching liquid is dipped into the cell 6 by suitable means such as a dropping pipette, and the matching liquid 8 is stirred to mix the two components. The liquid thus adjusted to define a refractive index $n_{m2}$ is the second matching liquid. If the refractive index $n_{m1}$ of the first matching liquid is somewhat larger than the refractive index $n_t$ of the test lens, the refractive index $n_{m2}$ of the second matching liquid is adjusted to be somewhat smaller than the refractive index $n_t$. Inversely, if $n_{m1}$ is somewhat smaller than $n_t$, $n_{m2}$ is adjusted to be somewhat larger than $n_t$.

Subsequently, in the same manner as in the first matching liquid, the refractive index $n_{m2}$ of the second matching liquid is determined from the interference fringe generated by the superposition between the light wave that has passed through the glass sample 9 and the reference light wave. The results are stored in the memory (8).

Then, in the same manner as in the first matching liquid, the fringe is generated by the superposition between the light wave that has passed through the test lens 10 and the reference light. FIG. 10A shows an example of the interference fringe 50 imaged on the imaging element 14. Then, from the output of the imaging element 14, the interference fringe is developed into a second polynominal $W_{o2}(X, Y)$ in the arithmetic circuit 16. Then, the defocus term and the aberration term of the polynominal are stored in the memory 18.

Subsequently, from the difference between the first and second polynominals $W_{o1}$, $W_{o2}$ and the difference in refractive indices $n_{m1}$, $n_{m2}$ between the first and second matching liquids, the Sag amount (i.e., shape) of the test lens is obtained as follows:

$$Sag(X, Y) = \frac{W_{01}(X, Y) - W_{02}(X, Y)}{n_{m2} - n_{m1}}$$

Then, the maximum Sag ($S_{o1}+S_{o2}$) is obtained. The refractive index $n_{m2}$ of the second matching liquid is read out from the memory 18. From the second defocus term of the second polynominal, the average refractive index $n_{to}$ of the test lens 10 is obtained as follows:

$$n_{to} = n_{m2} + \frac{\text{defocus term}}{S_{e1} + S_{e2}}$$

The result is outputted to be indicated in the indicator 17.

Also, from the memory 18, the thickness $[d - Sag(X, Y)]$ of each portion of the test lens 10 is read out. From the aberration term (W) of the second polynominal, the refractive index distribution $\Delta n_t (X, Y)$ of the test lens 10 is obtained as follows:

$$\Delta n_t(X, Y) = \frac{W(X, Y)}{d - Sag(X, Y)}$$

The result is outputted to be indicated in the indicator 17.

Incidentally, in the foregoing method, the defocus term and the aberration term of the second polynominal are stored in the memory 18 and are used for measurement analyses. It is, however, possible to use the first polynominal instead of the second polynominal. In this case, the average refractive index $n_{to}$ of the test lens 10 is given as follows:

$$n_{to} = n_{m1} + \frac{\text{defocus term of 1st polynominal}}{S_{e1} + S_{e2}}$$

where $n_{m1}$ is the refractive index of the first matching liquid.

According to the foregoing method, it is only necessary to dip the test lens into the matching liquid. Thus, there is no fear that the lens is damaged during the measurement. In addition, the defocus term is picked up to thereby the average refractive index of the lens having the unknown refractive index and shape. The refractive index distribution may be obtained from the aberration term of the polynominal. This leads to the automation of the numerical analyses of lenses.

Another embodiment will now be described with reference to FIGS. 14 and 15. As described above, $[n_{to}-n_m]$ is determined from the defocus terms $W_2$ in the observed (or read) fringe $W_o(x,y)$, and $\Delta n_t(x,y)$ is determined from aberration terms (W), thus making it possible to separate two parameters from each other.

Namely, if the defocus term is kept at zero, the components of the observed fringe only show the aberration term, i.e., the refractive index distribution, when $n_{to}-n_m=0$, that is, when the average refractive index $n_{to}$ of the lens to be inspected and the refractive index $n_m$ of the sample are identical with each other. According to this embodiment, by adjusting an expansion angle adjusting means, the fringe component generated due to the difference between the average refractive index $n_{r0}$ of the lens and the refractive index $n_m$ of the sample liquid is eliminated to keep the condition where $n_{r0}-n_m=0$. Therefore, at this time, it is possible to measure the refractive index distribution of the lens according to the condition of the interference fringe.

Figure 14:
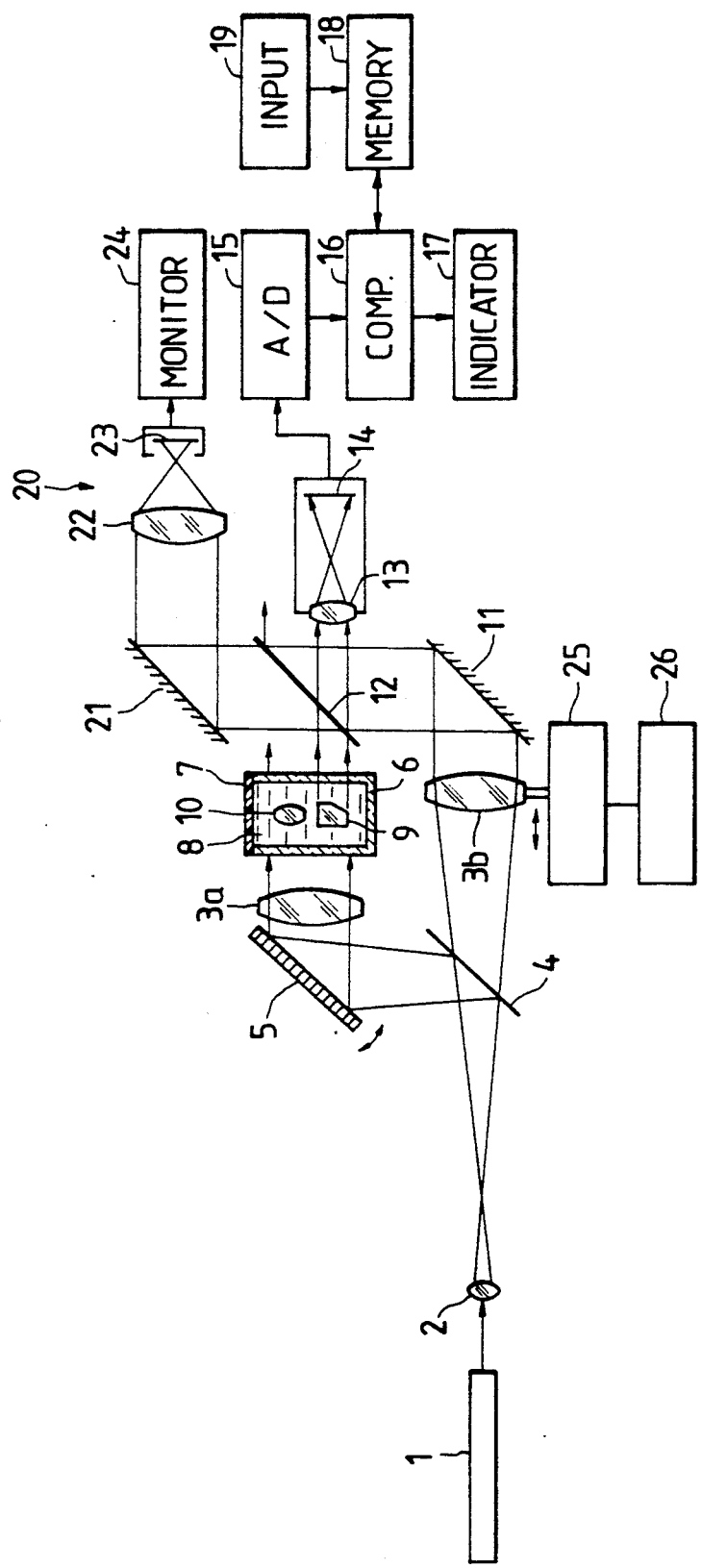
FIG. 14 is a diagram showing another method of measuring the refractive index of lenses.

FIG. 14 shows a measuring apparatus according to the invention, which also basically constitutes a Mach-Zehnder interferometer. A coherent light source 1 emits a coherent light (having a wavelength λ) and is composed of, for example, a He-Ne laser light source. The light beam limited from the coherent light source 1 is expanded by a beam expander 2 and is divided into a reflective light and a transmission light by a first half mirror f4. The light flux reflected by the half mirror 4 is further reflected by a movable mirror 5, and is adapted to pass through a transparent cell 6 while being transferred to parallel light by a first collimator lens 3a. The movable mirror 5 may be finely adjusted in angle as desired (tilt adjustment).

The transparent cell 6 is formed of glass having no distortion or warpage. The cell 6 is made in the same manner as in the foregoing embodiments.

A test lens 10 and a glass sample 9 having known refractive index ng and dimensions (θ, L) are set in the same manner as in the foregoing embodiments. Incidentally, the glass sample 9 is not necessary for measuring the refractive index but is needed for measuring the refractive index distribution.

The light flux that has passed through the first half mirror 4 is collimated into a parallel light by a collimator lens 3b and is reflected by a first fixed mirror 11. Then, the light is superposed with a light wave that has pass through the test lens 10 at a second half mirror 12. The superposition causes an interference fringe.

The second collimator lens 3b is provided with an angle fine adjustment means 25 for finely moving the second collimator lens 3b in the axial direction to finely adjust the light flux emitted from the collimator lens 3b from the parallel rays to the non-parallel rays. A movement detection means 26 for detecting the movement of the collimator lens 3b comprises a scale or the like.

According to the measuring method of the invention, in order to measure the refractive index distribution of the lens, the second collimator lens 3b is moved in the direction of the optical axis by the expansion angle fine adjustment means 25, thereby finely adjust the expansion angle of the emitted light from the collimator lens 3b. Then, the number of interference fringes observed in a monitoring indicator 24 is changed, the fringes disappear at a certain position, while local shades remain. In the case where the movable mirror 5 is tilted, as shown in FIG. 15, substantially straight parallel fringes are present in the central portion of the fringes and the fringes are bent in the marginal portions. Under this condition, the fringe components caused by the difference between the average refractive index $n_{r0}$ of the test lens 10 and the refractive index $n_m$ of the matching liquid 8 disappears. This condition is the same as expressed by $n_{r0}=n_m$. Namely, the defocus term is eliminated from the interference fringes but the aberration term, that is, the refractive index distribution is observed.

Figures 15, 16:
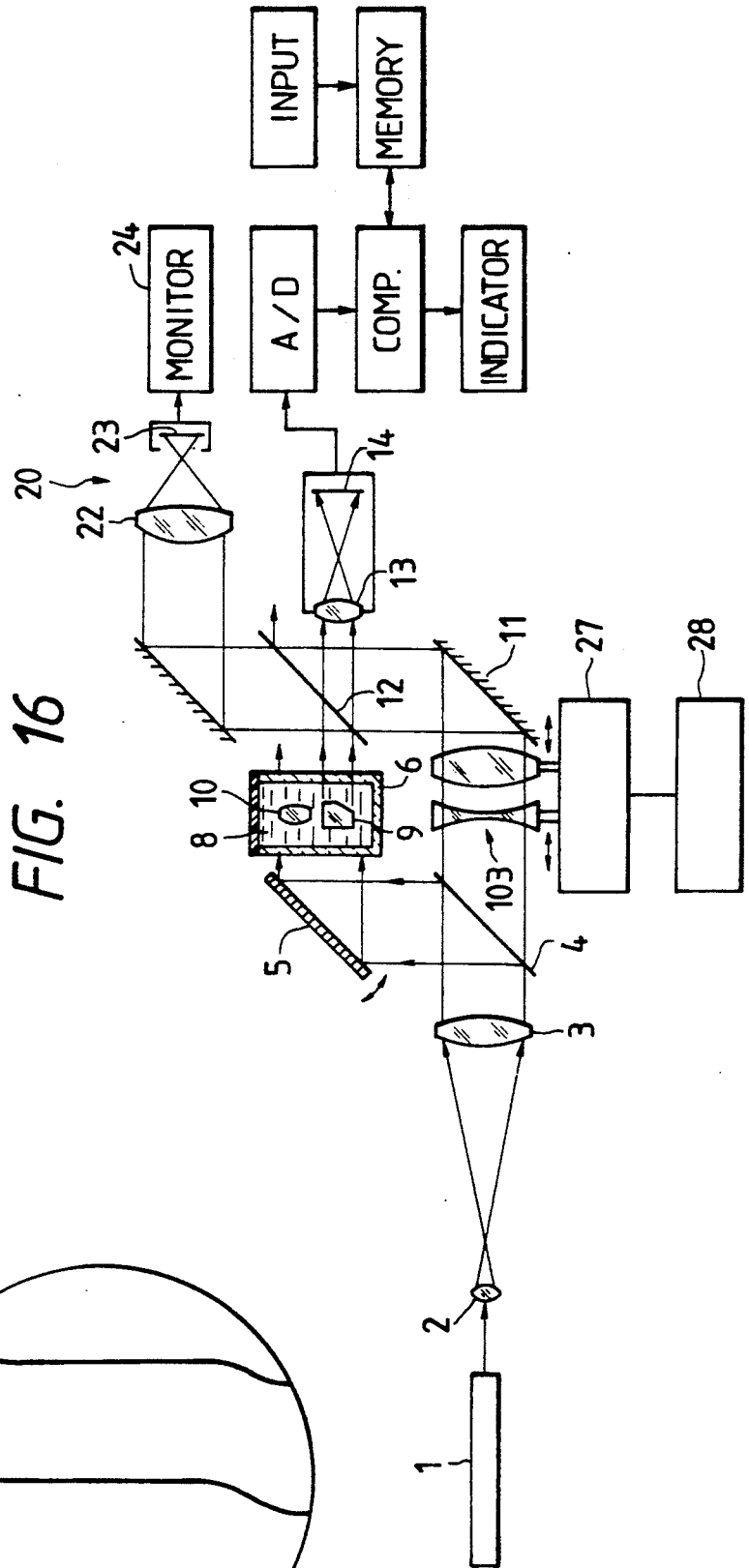
FIG. 15 is a diagram showing a fringe in connection with FIG. 14.
FIG. 16 is a diagram showing still another method of measuring the refractive index by using a zoom lens.

Therefore, it is possible to measure the maximum refractive index distribution and, and etc., of the test lens according to a magnitude s of offset in the marginal portions of the fringes shown in FIG. 15.

The other structure shown in FIG. 14 is substantially the same as shown in FIG. 4.

On the other hand, it is known by movement detector 26 how long the second collimator lens 3b is moved, from the condition where the parallel light is emitted from the second collimator lens 3b. It is also possible to determine the refractive index of the test lens 10 from the movement of the collimator lens 3b and the refractive index $n_m$ of the matching liquid 8.

Incidentally, in the foregoing embodiment, the movable mirror 5 may be tilted. However, instead thereof, the fixed mirror 11 may be movable to tilt. Also, to eliminate the defocus term components from the fringes, the first and second collimator lenses 3a and 3b may be both moved in a fine adjustment manner. Also, either first or second collimator lens may be moved. As shown in FIG. 16, a zoom lens 103 is disposed to change the focal length of the lens to adjust the expansion of the emitted light. As shown in FIG. 16, numeral 3 denotes a collimator lens; 27, an expansion angle fine adjustment means for driving the zoom lens 103; and 28, a focal length indicating means for indicating the focal length of the zoom lens 103.

According to this method, it is only necessary to dip the lens in the sample liquid for measuring the refractive index distribution of the lens through naked eyes without any calculation. It is therefore possible to inspect with ease the refractive index distribution of the lenses being manufactured. Accordingly, the product quality management may readily be performed at a high level.

An embodiment of the present invention is described hereinafter with reference to FIGS. 17 and 18.

Figure 17:
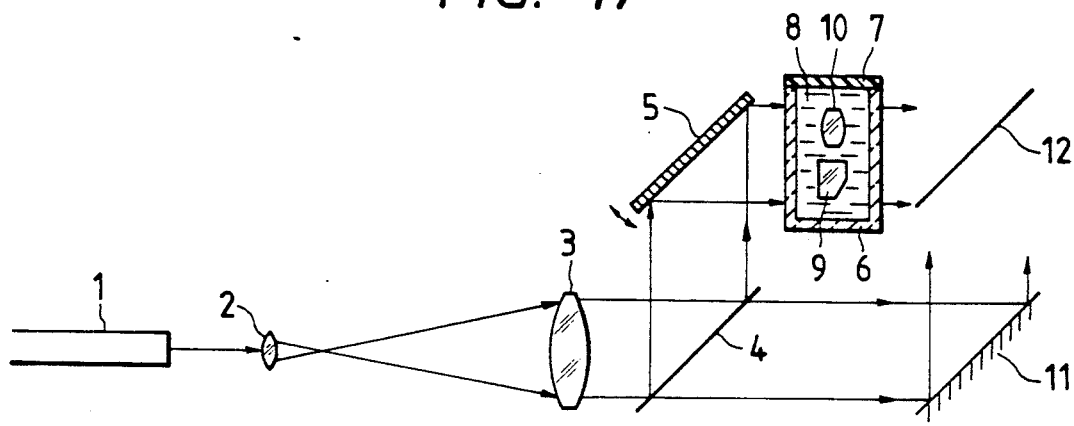
FIG. 17 is a diagram showing an example of an interferometer.
Figure 18:
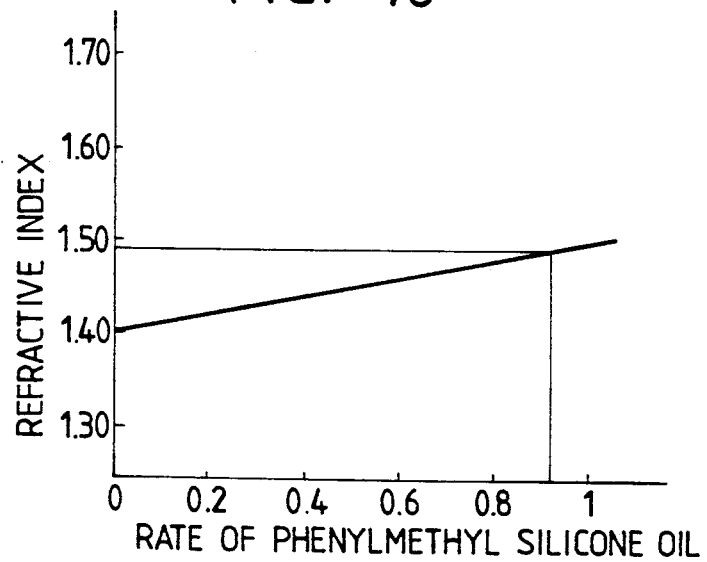
FIG. 18 is a graph showing the result of the example of FIG. 17.

FIG. 17 is a schematic diagram of an interferometer. Shown by 1 is a coherent light source which emits coherent light (wavelength, λ) and may be exemplified by a He-Ne laser light source. The rays of light emitted from the coherent light source 1 are expanded with a beam expander 2 and collimated with a collimator lens 3. The parallel beams of light are reflected from a first half mirror 4, thence reflected by a movable mirror 5 to be transmitted through a transparent cell 6. The movable mirror 5 is capable of tilting through a desired small angle.

The transparent cell 6 is made of undistorted glass and is furnished with a cover 7 that can be freely opened or closed. The cell 6 is filled with a matching fluid 8 prepared by mixing two kinds of liquid components, a dimethyl silicone oil and a phenylmethyl silicone oil.

Immersed within the matching fluid 8 are a glass sample 9 whose refractive index and shape are both known and an acrylic lens 10 which is an object under test in the example being discussed. The glass sample 9 and the acrylic lens 10 are juxtaposed in such a way that they are oriented perpendicular to the rays of light that pass through the transparent cell 6.

The rays of light that have passed through the first half mirror 4 are reflected from a first fixed mirror 11, thence reflected by a second half mirror 12, and superposed on the light wave that has passed through the lens under test 10 or the glass sample 9. Interference fringes will then form as a result of superposition of the two light waves and through their observation, optical parameters such as the refractive index of the lens 10 can be measured.

The procedure of measurement usually starts with adjusting the refractive index of the matching fluid to a value substantially equal to the refractive index of the lens under test 10. This may be done by the operator in such a way that the number of interference fringes that are produced with the light wave passing through the lens 10 will not exceed a certain value, say, three. More specifically, the cover 7 is removed from the cell 6, one of the two silicone oils that make up the matching fluid 8 is dripped into the cell 6 by suitable means such as a dropping pipette, and the matching fluid 8 is stirred to mix the two components.

In the embodiment discussed above, a single dimethyl silicone oil is mixed with a single phenylmethyl silicone oil to make up a matching fluid. However, this is not the sole applicable embodiment of the present invention and a plurality of dimethyl silicone oils having refractive indices within the range of 1.350–1.450 may be mixed with a plurality of phenylmethyl silicone oils having refractive indices within the range of 1.480–1.630 to make up matching fluids. The lens under test 10 also is not limited to those made of plastics alone and glass and other materials may be employed.

Experiment 4

Refractive index measurements were performed on matching fluids for varying ratios of dimethyl silicone oil having a refractive index of 1.399 to a phenylmethyl silicone oil having a refractive index of 1.499. The results are shown in FIG. 18, from which one can see that the refractive index of matching fluids varies in proportion to the mixing ratio of phenylmethyl silicone oil to dimethyl silicone oil. FIG. 18 also shows that in order to make a matching fluid having a refractive index of 1.491 which is equal to that of polymethyl methacrylate, the mixing ratio of dimethylsilicone oil to phenylmethyl silicone oil need be adjusted to 8:92. The variation in the refractive index of matching fluids with temperature was negligible.

Experiment 5

Matching fluids were prepared from various combinations of dimethyl silicone oils and phenylmethyl silicone oils. Glass and acrylic lenses were immersed in the prepared matching fluids but in no case were they attacked by the matching fluids.

In contrast, a matching fluid made by mixing clove oil and butanol, which were known to have good optical characteristics, severely eroded the surface of the acrylic lenses.

Experiment 6

Matching fluids were prepared by mixing various combinations of dimethyl silicone oils and phenylmethyl silicone oils with stirring. Using these matching fluids, interference fringes were produced and observed with an interferometer of the type shown in FIG. 17. Uniform interference fringes were observed in every instance, and this indicates the fact that the silicone oils were mixed in an optically uniform and consistent manner in the matching fluids.

In contrast, the interference fringes produced with a matching fluid prepared by mixing with stirring heptane and a silicone oil which are said to be highly miscible with each other formed a complicated pattern, indicating that the two liquid components did not mix into a completely homogeneous state.

In accordance with the present invention, an improved matching fluid can be obtained by mixing one or more dimethyl silicone oils with one or more phenylmethyl silicone oils. This matching fluid will not attack acrylics or any other plastic material. In addition, it is an optically stable fluid that is capable of providing desired refractive indices over a broad range. An interferometer using this matching fluid is capable of accomplishing easy and precise optical measurements on various materials including plastics and glass.

Another method for measuring a refractive index of the matching liquid 8 according to the invention will now be described referring back to FIGS. 4 to 9. In order to measure the refractive index of the matching liquid 8, the known data are inputted into the input circuit 19. The data concerning the glass sample 9 ($n_g$, $\theta$, L) are stored into the memory 18.

Subsequently, as shown in FIG. 6, the first imaging lens 13 is confronted with the glass sample 9. Then, as shown in FIG. 7, the interference fringes 30 generated by the superposition of the light wave that has passed through the glass sample 9 and the reference light wave are imaged on the imaging element 14. Then, by the output of the imaging element 14, the spatial frequency F of the fringes is calculated in the arithmetic circuit 16.

In this case, first of all, the intensity distribution of the segment 31 as shown in FIG. 8 is measured. FIG. 9 shows the intensity distribution on the segment 31 in the form of a sine curve.

Figure 19:
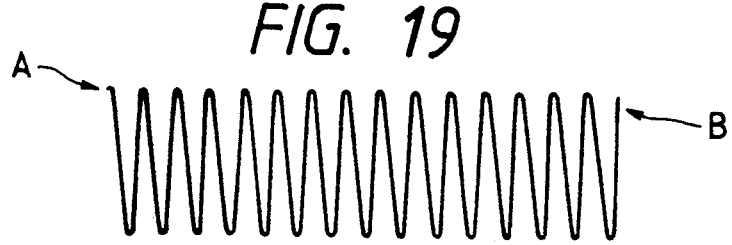
FIG. 19 is a diagram showing a sine curve of intensity distribution in which points A and B are displaced from each other.

The thus measured data concerning the intensity distribution is finite on the segment 31. Therefore, assuming that such an intensity distribution be continued infinitely, Fourier calculations are performed in accordance with FFT to obtain the spatial frequency F. In this case, if the starting point A and the terminal point B of the wave forms of the intensity distribution on the segment 31 are identical with each other, it is convenient that the curves are contiguous with each other when developed infinitely. However, if the starting point A and the terminal point B are not identical with each other as shown in FIG. 19, the curves are discontinuous at the joint portion. If this is Fourier transformed, high order components will be produced to cause errors. Therefore, in order to obtain the frequency, a so-called "window function" is used to remove the high order components. Also if discrete Fourier transformation is performed, a quantity errors will necessarily be produced. It is inevitable to avoid the errors corresponding to 0.5 fringe. Accordingly, in the frequency region, if the detection of the peak of the magnitude is obtained by simulating with a secondary function, it is possible to reduce the errors by about half.

Including such a correction, the frequency F of the interference fringe is obtained by the arithmetic circuit 16. Then, $n_g$, $\theta$ and L are read out from the memory 18, and subsequently, the refractive index of the matching liquid 8 is obtained in accordance with $n_m = n_g + \lambda F / \tan\theta$, and the result is indicated to the indicator 17.

In order to achieve the optical measurement of the test lens 10, the first imaging lens 13 is moved to a position confronted with the test lens 10.

According to this method, since the refractive index of the sample liquid is obtained from the spatial frequency of the interference fringe generated by projection of the coherent light to the sample liquid, it is possible to perform a numerical measurement, which leads to an automatic measurement with ease. Also, since it is possible to measure the refractive index while using the liquid in the interferometer in a real time manner, the precision in optical measurement by using the interferometer may be enhanced.

We claim:

1. A method of measuring a refractive index distribution of a lens, comprising the following steps: immersing a glass sample and a lens under test within a matching fluid whose refractive index differs slightly from that of the lens to be tested, said glass sample having a refractive index and a shape which are both known and said lens to be tested having an unknown refractive index but a known shape; allowing coherent light to pass through said glass sample and said lens under test; superposing the transmitted light wave on a reference light wave to generate interference fringes; outputting the intensity distribution of interference fringes that are generated by the light wave that has passed through said glass sample; determining the refractive index of said matching fluid on the basis of the resulting output; outputting the intensity distribution of interference fringes that are generated by the light wave that has passed through said lens under test; separating from the resulting output the defocus term and aberration terms in the polynomial which expresses the produced interference fringes; determining the average refractive index of said lens under test from the separated defocus term and the refractive index of the matching fluid; and determining the refractive index distribution of said lens under test from said aberrations terms.

2. A method of measuring the refractive index of a lens comprising the following steps: immersing in a first matching fluid a glass sample having a refractive index and a shape which are both known and a lens under test whose refractive index and shape are both unknown; allowing coherent light to pass through said glass sample and said lens under test; superposing the transmitted light wave on a reference light wave to generate interference fringes; outputting the intensity distribution of interference fringes that are generated by the light wave that has passed through said glass sample; determining the refractive index of said first matching fluid on the basis of the resulting output; outputting the intensity distribution of interference fringes that are generated by the light wave that has passed through said lens under test; determining from the resulting output a first polynomial that expresses said interference fringes; subsequently immersing said glass sample and said lens under test in a second matching fluid having a refractive index slightly different from that of the first matching fluid; allowing said coherent light to pass through said glass sample and said lens under test; superposing the transmitted light wave on reference light wave to generate interference fringes; outputting the intensity distribution of interference fringes that are generated by the light wave that has passed through said glass sample; determining the refractive index of said second matching fluid on the basis of the resulting output; outputting the intensity distribution of interference fringes that are generated by the light wave that has passed through said lens under test; determining from the resulting output a second polynomial that expresses said interference fringes; determining the shape of said lens under test from the refractive indices of the first and second matching fluids using the first and second polynomials; separating the defocus term from the aberration terms in said first or second polynomial; determining the average refractive index of said lens under test from the separated defocus term and from the refractive index of said first or second matching fluid; and determining the refractive index distribution of said lens under test from said aberration terms.

3. A method of measuring a refractive index distribution of a lens, in an interferometer wherein a lens under test is immersed into sample liquid whose refractive index differs slightly from that of the test lens, and coherent light is allowed to pass through said test lens to superpose with reference light to form a fringe, said method characterized by comprising:
providing in said interferometer a fine angular adjustment means for finely adjusting an expansion angle for at least one of transmitted light and reference light from parallel beam to non-parallel beam;
adjusting said fine angular adjustment means to eliminate fringe components generated due to a difference between refractive index of said test lens and refractive index of said sample liquid; and
measuring refractive index of said test lens in accordance with a condition of the interference fringe measured in said adjusting step.

4. A matching fluid consisting of one or more dimethyl silicone oils having refractive indices within the range of 1.350–1.450 which are mixed with one or more phenylmethyl silicone oils having refractive indices within the range of 1.480–1.630.

5. An interferometer comprising:
a matching fluid consisting of one or more dimethyl silicone oils having refractive indices within the range of 1.350–1.450 which are mixed with one or more phenylmethyl silicone oils having refractive indices within the range of 1.480–1.630;
a transparent cell for accommodating said matching fluid in which an object under test is to be immersed;
coherent light illuminating means that illuminates said transparent cell with coherent light; and
reference light illuminating means that provides an illumination of reference light in such a way that it is superposed on the coherent light passing through said transparent cell.

6. A method of measuring refractive index of sample liquid, comprising the steps of:
immersing into sample liquid a transparent sample whose refractive index and shape are known;
allowing coherent light to pass through said transparent sample to be superposed with reference light to generate an interference fringe;
measuring an intensity distribution in brightness of said interference fringe;
obtaining a spatial frequency of said interference fringe according to said intensity distribution; and
obtaining refractive index of said sample liquid according to the known refractive index and shape of said transparent sample and spatial frequency of interference fringe.

7. An apparatus for measuring a refractive index distribution of a lens, comprising:
means for immersing a glass sample and a lens under test within a matching fluid whose refractive index differs slightly from that of the lens to be tested;
means for allowing coherent light to pass through said glass sample and said lens under test;
means for superposing the transmitted light wave on reference light wave to generate interference fringes; first means for outputting the intensity distribution of interference fringes that are generated by the light wave that has passed through said glass sample;
means for determining the refractive index of said matching fluid on the basis of an output of said outputting means; second means for outputting the intensity distribution of interference fringes that are generated by the light wave that has passed through said lens under test;

means for separating from the resulting output the defocus term and aberration terms in the polynomial which expresses the produced interference fringes;

means for determining the average refractive index of said lens under test from the separated defocus term and the refractive index of the matching fluid; and means for determining the refractive index distribution of said lens under test from said aberration terms.

8. An apparatus for measuring the refractive index of a lens comprising:

means for immersing in a first matching fluid a glass sample having a refractive index and a shape which are both known and a lens under test whose refractive index and shape are both unknown;

means for allowing coherent light to pass through said glass sample and said lens under test; means for superposing the transmitted light wave on reference light wave to generate interference fringes;

first means for outputting the intensity distribution of interference fringes that are generated by the light wave that has passed through said glass sample;

means for determining the refractive index of said first matching fluid on the basis of an output of said first outputting means;

second means for outputting the intensity distribution of interference fringes that are generated by the light wave that has passed through said lens under test;

means for determining from the resulting output a first polynomial that expresses said interference fringes and for subsequently immersing said glass sample and said lens under test in a second matching fluid having a refractive index slightly different from that of the first matching fluid;

means for allowing said coherent light to pass through said glass sample and said lens under test;

means for superposing the transmitted light wave on a reference light wave to generate interference fringes;

means for outputting the intensity distribution of interference fringes that are generated by the light wave that has passed through said glass sample;

means for determining the refractive index of said second matching fluid on the basis of the resulting output;

means for outputting the intensity distribution of interference fringes that are generated by the light wave that has passed through said lens under test;

means for determining from the resulting output a second polynomial that expresses said interference fringes;

means for determining the shape of said lens under test from the refractive indices of the first and second matching fluids using the first and second polynomials;

means for separating the defocus term from the aberration terms in said first or second polynomial; determining the average refractive index of said lens under test from the separated defocus term and from the refractive index of said first or second matching fluid; and means for determining the refractive index distribution of said lens under test from said aberration terms.

9. An apparatus for measuring a refractive index distribution of a lens, in an interferometer wherein a lens under test is immersed into sample liquid whose refractive index differs slightly from that of the test lens, and coherent light is allowed to pass through said test lens to superpose with reference light to form a fringe, said apparatus characterized by comprising:

means for providing in said interferometer a fine angular adjustment means for finely adjusting an expansion angle for at least one of transmitted light and reference light from parallel beam to non-parallel beam;

means for adjusting said fine angular adjustment means to eliminate fringe components generated due to a difference between refractive index of said test lens and refractive index of said sample liquid; and means for measuring a refractive index of said test lens in accordance with a condition of the interference fringe measured in said adjusting step.

10. An apparatus for measuring refractive index of sample liquid, comprising the steps of:

means for immersing into sample liquid a transparent sample whose refractive index and shape are known;

means for allowing coherent light to pass through said transparent sample to be superposed with reference light to generate an interference fringe;

means for measuring an intensity distribution in brightness of said interference fringe;

means for obtaining a spatial frequency of said interference fringe according to said intensity distribution; and means for obtaining a refractive index of said sample liquid according to the known refractive index and a shape of said transparent sample and spatial frequency of the interference fringe.

11. A method of measuring refractive index of sample liquid, comprising the steps of:

immersing into sample liquid a transparent sample whose refractive index and shape are known;

allowing coherent light to pass through said transparent sample to be superposed with reference light to generate an interference fringe;

measuring an intensity distribution in brightness of said interference fringe;

obtaining a spatial frequency of said interference fringe according to said intensity distribution; and obtaining refractive index of said sample liquid according to the known refractive index and shape of said transparent sample and spatial frequency of interference fringe.

12. The method according to claim 11, wherein said transparent sample is in the form of a wedge.

13. An apparatus for measuring a refractive index distribution of a lens, comprising:

means for immersing a glass sample and a lens under test within a matching fluid whose refractive index differs slightly from that of the lens to be tested;

means for allowing coherent light to pass through said glass sample and said lens under test;

means for superposing the transmitted light wave on reference light wave to generate interference fringes; first means for outputting the intensity distribution of interference fringes that are generated by the light wave that has passed through said glass sample;

means for determining the refractive index of said matching fluid on the basis of an output of said outputting means; second means for outputting the intensity distribution of interference fringes that are generated by the light wave that has passed through said lens under test;

means for separating from the resulting output the defocus term and aberration terms in the polynomial which expresses the produced interference fringes;

means for determining the average refractive index of said lens under test from the separated defocus term and the refractive index of the matching fluid; and means for determining the refractive index distribution of said lens under test from said aberration terms.

14. An apparatus for measuring the refractive index of a lens comprising:

means for immersing in a first matching fluid a glass sample having a refractive index and a shape which are both known and a lens under test whose refractive index and shape are both unknown;

means for allowing coherent light to pass through said glass sample and said lens under test; means for superposing the transmitted light wave on reference light wave to generate interference fringes;

first means for outputting the intensity distribution of interference fringes that are generated by the light wave that has passed through said glass sample;

means for determining the refractive index of said first matching fluid on the basis of an output of said first outputting means;

second means for outputting the intensity distribution of interference fringes that are generated by the light wave that has passed through said lens under test;

means for determining from the resulting output a first polynomial that expresses said interference fringes and for subsequently immersing said glass sample and said lens under test in a second matching fluid having a refractive index slightly different from that of the first matching fluid;

means for allowing said coherent light to pass through said glass sample and said lens under test;

means for superposing the transmitted light wave on a reference light wave to generate interference fringes;

means for outputting the intensity distribution of interference fringes that are generated by the light wave that has passed through said glass sample; means for determining the refractive index of said second matching fluid on the basis of the resulting output;

means for outputting the intensity distribution of interference fringes that are generated by the light wave that has passed through said lens under test; means for determining from the resulting output a second polynomial that expresses said interference fringes;

means for determining the shape of said lens under test from the refractive indices of the first and second matching fluids using the first and second polynomials;

means for separating the defocus term from the aberration terms in said first or second polynomial;

determining the average refractive index of said lens under test from the separated defocus term and from the refractive index of said first or second matching fluid; and means for determining the refractive index distribution of said lens under test from said aberration terms.

15. An apparatus for measuring a refractive index distribution of a lens, in an interferometer wherein a lens under test is immersed into sample liquid whose refractive index differs slightly from that of the test lens, and coherent light is allowed to pass through said test lens to superpose with reference light to form a fringe, said apparatus characterized by comprising:

means for providing in said interferometer a fine angular adjustment means for finely adjusting an expansion angle for at least one of transmitted light and reference light from parallel beam to non-parallel beam;

means for adjusting said fine angular adjustment means to eliminate fringe components generated due to a difference between refractive index of said test lens and refractive index of said sample liquid; and means for measuring a refractive index of said test lens in accordance with a condition of the interference fringe measured in said adjusting step.

16. An apparatus for measuring refractive index of sample liquid, comprising the steps of:

means for immersing into sample liquid a transparent sample whose refractive index and shape are known;

means for allowing coherent light to pass through said transparent sample to be superposed with reference light to generate an interference fringe;

means for measuring an intensity distribution in brightness of said interference fringe;

means for obtaining a spatial frequency of said interference fringe according to said intensity distribution; and means for obtaining a refractive index of said sample liquid according to the known refractive index and shape of said transparent sample and spatial frequency of the interference fringe.

17. A method of measuring an optical factor, said method comprising the steps of:

immersing a reference sample and an optical sample under test within a matching fluid whose refractive index differs from that of the optical sample to be tested, said reference sample having a refractive index and a shape which are both known and said optical sample to be tested having an unknown refractive index but a known shape;

passing coherent light through said reference sample and said optical sample under test;

superposing the transmitted light wave on a reference light wave to generate interference fringes;

providing a resulting output representing an intensity distribution of interference fringes that are generated by the light wave that has passed through said reference sample; and determining the refractive index of said matching fluid based on the resulting output.

18. The method according to claim 17, wherein said reference sample comprises a glass sample.

19. The method according to claim 17, wherein said optical sample comprises a lens.

20. The method according to claim 17, wherein said resulting output comprises a polynomial having a defocus term and aberration terms, and wherein said determining step comprises the step of separating the defocus term and aberration terms from said polynomial.

21. The method according to claim 20, wherein said resulting output specifies said shape of said optical sample in terms which include an amount of maximum sag.

22. The method according to claim 17, further comprising the steps of:
providing a second resulting output representing an intensity distribution of said interference fringes that are generated by the light wave that has passed through said optical sample under test, said second resulting output having a defocus term; and
determining the average refractive index of said optical sample from said defocus term and said refractive index of said matching fluid.

23. The method according to claim 22, wherein said resulting output specifies said shape of said optical sample in terms which include an amount of maximum sag.

24. The method according to claim 22, wherein the defocus term is part of a polynomial which expresses the produced interference fringes.

25. The method according to claim 24, wherein the polynomial is a Zernike's polynomial.

26. The method according to claim 22, further comprising the step of determining the refractive index distribution of said optical sample in accordance with an aberration term included in said second resulting output.

27. The method according to claim 17, further comprising the steps of:
providing a second resulting output representing an intensity distribution of said interference fringes that are generated by the light wave that has passed through said optical sample under test said second resulting output having an aberration term; and
determining the refractive index distribution of said optical sample under test from said aberration term.

28. The method according to claim 27, wherein the defocus term is part of a polynomial which expresses the produced interference fringes.

29. The method according to claim 28, wherein the polynomial is a Zernike's polynomial.

30. A method of measuring an optical factor, said method comprising the steps of:
immersing in a first matching fluid a reference sample having a refractive index and a shape which are both known and an optical sample under test whose refractive index and shape are both unknown;
passing coherent light through said reference sample and said optical sample under test;
superposing the transmitted light wave on a reference light wave to generate first interference fringes;
providing a first resulting output representing an intensity distribution of those of said first interference fringes that are generated by the light wave that has passed through said reference sample;
determining the refractive index of said first matching fluid based on said first resulting output;
immersing said reference sample and said optical sample under test in a second matching fluid having a refractive index different from that of the first matching fluid;
passing said coherent light through said reference sample and said optical sample under test;
superposing the transmitted light wave on a reference light wave to generate second interference fringes;
providing a second resulting output representing an intensity distribution of those of said second interference fringes that are generated by the light wave that has passed through said reference sample; and
determining the refractive index of said second matching fluid on the basis of the second resulting output.

31. An appartus for measuring an optical factor, said apparatus comprising:
means for immersing a reference sample and an optical sample under test within a matching fluid whose refractive index differs from that of the optical sample to be tested, said reference sample having a refractive index and a shape which are both known and said optical sample to be tested having an unknown refractive index but a known shape;
means for passing coherent light through said reference sample and said optical sample under test;
means for superposing the transmitted light wave on a reference light wave to generate interference fringes;
means for providing a resulting output representing an intensity distribution of those of said interference fringes that are generated by the light wave that has passed through said reference sample; and
means for determining the refractive index of said matching fluid based on the resulting output.

32. The apparatus according to claim 31, further comprising:
means for providing a second resulting output representing an intensity distribution of those of said interference fringes that are generated by the light wave that has passed through said optical sample under test; and
means for determining the average refractive index of said optical sample from the first or second resulting outputs.

33. The apparatus according to claim 32, further comprising means for determining the refractive index distribution of said optical sample under test from said second resulting output.

34. The apparatus according to claim 32, wherein said resulting output specifies said shape of said optical sample in terms which include an amount of maximum sag.

35. The method according to claim 32, wherein said second resulting output specifies said shape of said optical sample in terms including an amount of maximum sag.

36. The apparatus according to claim 31, wherein said reference sample comprises a glass sample.

37. The apparatus according to claim 31, wherein said optical sample comprises a lens.

38. The apparatus according to claim 31, wherein said first and second resulting outputs comprise polynomials each having defocus term and aberration terms, and wherein said means for determining comprises means for separating from the resulting output the defocus term and aberration terms in said polynomial.

39. An apparatus for measuring an optical factor, said apparatus comprising:
means for immersing in a first matching fluid a reference sample having a refractive index and a shape which are both known and an optical sample under test whose refractive index and shape are both unknown;

means for passing coherent light through said reference sample and said optical sample under test;
means for superposing the transmitted light wave on a reference light wave to generate first interference fringes;
means for providing a first resulting output representing an intensity distribution of those of said first interference fringes that are generated by the light wave that has passed through said reference sample;
means for determining the refractive index of said first matching fluid based on the first resulting output;
means for immersing said reference sample and said optical sample under test in a second matching fluid having a refractive index different from that of the first matching fluid;
means for passing said coherent light through said reference sample and said optical sample under test;
means for superposing the transmitted light wave on a reference light wave to generate second interference fringes;
means for providing a second resulting output representing an intensity distribution of those of said second interference fringes that are generated by the light wave that has passed through said reference sample;
means for determining the refractive index of said second matching fluid on the basis of the second resulting output.

* * * * *